(12) United States Patent
Voor

(10) Patent No.: US 9,452,003 B2
(45) Date of Patent: Sep. 27, 2016

(54) DEVICE AND METHOD TO PREVENT HIP FRACTURES

(75) Inventor: Michael J. Voor, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 154 days.

(21) Appl. No.: 12/508,350

(22) Filed: Jul. 23, 2009

(65) Prior Publication Data

US 2010/0023012 A1   Jan. 28, 2010

Related U.S. Application Data

(60) Provisional application No. 61/082,848, filed on Jul. 23, 2008.

(51) Int. Cl.
   *A61B 17/74* (2006.01)
(52) U.S. Cl.
   CPC .............. *A61B 17/74* (2013.01); *A61B 17/742* (2013.01)
(58) Field of Classification Search
   CPC .............................. A61B 17/74; A61B 17/742
   USPC ....................................................... 606/60–68
   See application file for complete search history.

(56) References Cited

U.S. PATENT DOCUMENTS

| | | | |
|---|---|---|---|
| 2,077,804 A | 4/1937 | Morrison | |
| 2,381,050 A | 8/1945 | Hardinge | |
| 3,716,051 A | 2/1973 | Fischer | |
| 3,759,257 A | 9/1973 | Fischer | |
| 3,805,775 A | 4/1974 | Fischer | |
| 4,236,512 A | 12/1980 | Aginsky | |
| 4,275,717 A | 6/1981 | Bolesky | |
| 4,339,217 A | 7/1982 | Lacey | |
| 4,379,451 A | 4/1983 | Getscher | |
| 4,409,974 A | 10/1983 | Freedland | |
| 4,432,358 A | 2/1984 | Fixel | |
| 4,519,100 A | 5/1985 | Wills et al. | |
| 4,632,101 A * | 12/1986 | Freedland | ........................ 606/68 |
| 4,721,103 A * | 1/1988 | Freedland | .................... 606/319 |
| 4,969,887 A | 11/1990 | Sodhi | |

(Continued)

FOREIGN PATENT DOCUMENTS

| | | |
|---|---|---|
| GB | 1436546 A | 5/1976 |
| WO | 2007-046691 | 4/2007 |
| WO | 2007046691 A1 | 4/2007 |

OTHER PUBLICATIONS

Pulkkinen et al., "Association of Geometric Factors and Failure Load Level With the Distribution of Cervical vs. Trochanteric Hip Fractures," Journal of Bone and Mineral Research, 2006, vol. 21, No. 6, pp. 895-901.

(Continued)

*Primary Examiner* — Nicholas Plionis
(74) *Attorney, Agent, or Firm* — Stites & Harbison, PLLC; Terry L. Wright; David W. Nagle, Jr.

(57) ABSTRACT

A device for preventing a hip fracture includes: a shaft having a first end and a second end and an expanding means for engaging the femoral head at the first end. The shaft is positioned in a hole of a predetermined depth in a femur. The hole extends from the greater trochanter to the femoral head of the femur, such that the first end is positioned in the femoral head and the second end is positioned in the greater trochanter. The device is oriented substantially perpendicular to the long axis of the femoral shaft.

8 Claims, 17 Drawing Sheets

(56) References Cited

U.S. PATENT DOCUMENTS

| | | | |
|---|---|---|---|
| 5,259,714 A | 11/1993 | Campbell | |
| 5,281,225 A * | 1/1994 | Vicenzi | 606/62 |
| 5,741,282 A | 4/1998 | Anspach et al. | |
| 5,759,184 A * | 6/1998 | Santangelo | 606/68 |
| 5,810,820 A | 9/1998 | Santori et al. | |
| 5,976,139 A | 11/1999 | Bramlet et al. | |
| 6,443,954 B1 | 9/2002 | Bramlet et al. | |
| 6,679,890 B2 | 1/2004 | Margulies et al. | |
| 6,685,706 B2 | 2/2004 | Padget et al. | |
| 6,783,530 B1 * | 8/2004 | Levy | 606/63 |
| 7,094,236 B2 | 8/2006 | Waisman | |
| 7,780,710 B2 * | 8/2010 | Orbay et al. | 606/286 |
| 7,828,802 B2 * | 11/2010 | Levy et al. | 606/63 |
| 7,914,533 B2 * | 3/2011 | Nelson et al. | 606/64 |
| 2001/0000186 A1 | 4/2001 | Bramlet et al. | |
| 2003/0078581 A1 | 4/2003 | Frei et al. | |
| 2003/0130660 A1* | 7/2003 | Levy et al. | 606/63 |
| 2005/0228391 A1* | 10/2005 | Levy et al. | 606/86 |
| 2006/0241606 A1 | 10/2006 | Vachtenberg et al. | |
| 2007/0046691 A1 | 3/2007 | Presley et al. | |
| 2008/0188897 A1* | 8/2008 | Krebs et al. | 606/300 |
| 2008/0255560 A1* | 10/2008 | Myers et al. | 606/63 |
| 2009/0005782 A1* | 1/2009 | Chirico et al. | 606/63 |
| 2009/0048672 A1* | 2/2009 | Essenmacher | 623/11.11 |
| 2009/0076607 A1* | 3/2009 | Aalsma et al. | 623/17.16 |
| 2010/0023010 A1 | 1/2010 | Nelson et al. | |
| 2010/0286692 A1* | 11/2010 | Greenhalgh et al. | 606/63 |

OTHER PUBLICATIONS

The International Bureau of WIPO, International Preliminary Report on Patentability for corresponding international patent application No. PCT/US2009/051571, issued Jan. 25, 2011.

Korean Intellectual Property Office, International Search Report and Written Opinion for corresponding international application PCT/US2009/051571, mailed Feb. 17, 2010.

Intellectual Property Office of New Zealand, Examination Report issued in corresponding application No. 591219, issued Jan. 27, 2012.

The State Intellectual Property Office of China, First Office Action issued in corresponding application No. 200980134279.X, issued Sep. 24, 2012.

European Patent Office, Supplementary European Search Report and Opinion, from Corresponding European Application No. 09801016.8, dated Feb. 13, 2014.

* cited by examiner

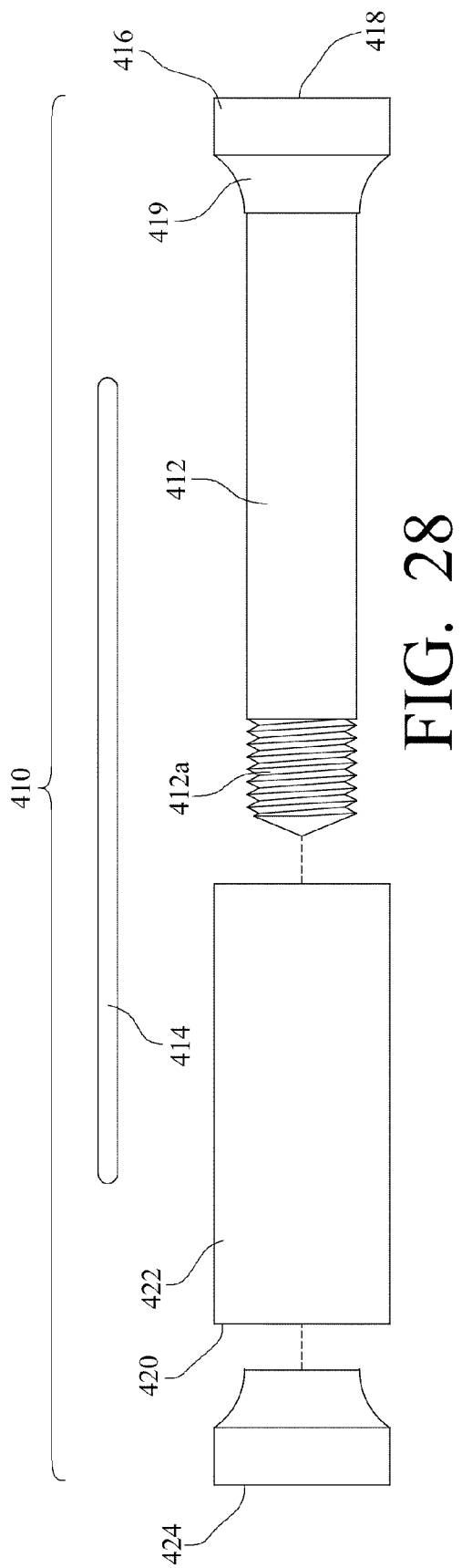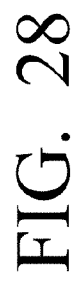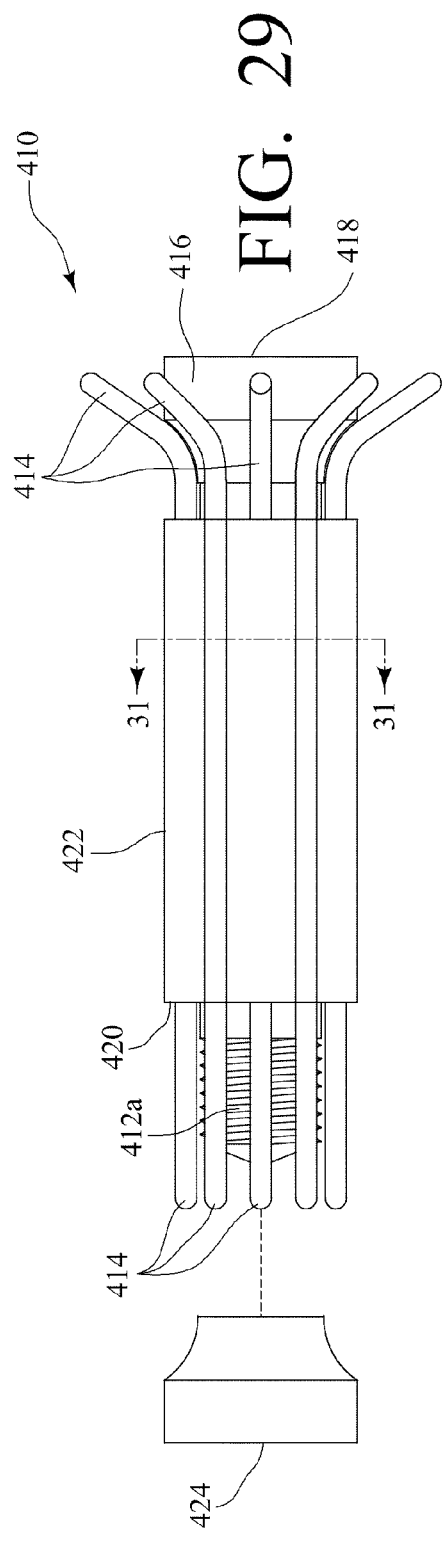

DEVICE AND METHOD TO PREVENT HIP FRACTURES

CROSS-REFERENCE TO RELATED APPLICATIONS

This application claims priority to U.S. Provisional Patent Application No. 61/082,848 filed on Jul. 23, 2008, the entire disclosure of which is incorporated herein by reference.

BACKGROUND OF THE INVENTION

The present invention relates to a device and method to prevent hip fractures.

The femur is the longest and largest bone in the human body. The femur forms part of the hip at one end and part of the knee at the other end. FIG. 1 is a front view of the upper portion of a femur, illustrating the various parts or areas of the femur 40, including the femoral head 42, the femoral neck 44, and the greater trochanter 46.

The femoral head 42 is generally globular and is directed upward, medialward, and a little forward, with the greater part of its convexity being above and in front. See Gray, Henry. *Anatomy of the Human Body.* Philadelphia: Lea & Febiger, 1918; Bartleby.com, 2000.

The femoral neck 44 is a truncated conical process of bone, connecting the femoral head 42 with the rest of the femur 40, and forming with the latter a wide angle opening medialward. Id. The femoral neck 44 is contracted in the middle and is broader laterally than medially. Id. The upper or superior border 45 of the neck 44 is short and thick, and ends laterally at the greater trochanter 46. Id. The inferior border, long and narrow, curves a little backward, to end at the lesser trochanter. Id.

The greater trochanter 46 is a large, irregular, quadrilateral eminence, situated at the junction of the neck 44 with the upper part of the femur 40. Id. The greater trochanter 46 has two surfaces and four borders. Id. The lateral surface, quadrilateral in form, is broad, rough, convex, and marked by a diagonal impression, which extends from the postero-superior to the antero-inferior angle. Id. The medial surface, of much less extent than the lateral, presents at its base a deep depression, the trochanteric fossa (digital fossa). Id. The superior border is free; it is thick and irregular, and marked near the center by an impression. Id. The inferior border corresponds to the line of junction of the base of the trochanter with the lateral surface of the body; it is marked by a rough, prominent, slightly curved ridge. Id. The anterior border is prominent and somewhat irregular. Id. The posterior border is very prominent and appears as a free, rounded edge, which bounds the back part of the trochanteric fossa. Id.

The femoral shaft 47 is generally cylindrical. Id. The femoral shaft 47 is slightly arched, so as to be convex in front, and concave behind, where it is strengthened by a prominent longitudinal ridge, the linea aspera. Id.

FIG. 1 also illustrates the axis of the normal load-bearing vector 48, i.e., the axis upon which loads act during walking, standing, and other activities of daily living. FIG. 1 further illustrates the general orientation of the longitudinal axis 50 of the femoral neck 44, along with the long axis 52 of the femoral shaft 47 of the femur 40.

Referring now to FIGS. 2-5, hip fractures commonly result from a fall to the side in which impact with the ground occurs over the greater trochanter 46 of the lateral femur 40. During a hip fracture, the impact from a fall to the side (as best shown in FIG. 2) results in a three-point bending of the femur 40, including a "reverse bending" load on the femoral neck 44 with the upper (or superior) border or side 45 of the femoral neck 44 developing a compressive stress and the lower (or inferior) border or side 49 of the femoral neck 44 developing a tensile stress. It is believed that the weaker upper border or side 45 of the femoral neck 44 most likely fails or cracks first in compression, as indicated by reference numeral 56 in FIG. 3. After the initial failure, the crack propagates across the entire femoral neck 44, including the stronger lower side 45 where the predominant load is tension/bending, as shown in FIG. 4. Finally, depending on the direction of the crack propagation, this culminates in a hip fracture, either as a neck fracture 58 or an intertrochanteric fracture 60, as shown in FIG. 5.

For further information about the mechanics of hip fracture, see Turner, C H. The Biomechanics of Hip Fracture. *Lancet.* 2005 July 9-15;366(9480):98-9. See also Mansek, Sarah et al. Failure in Femoral Neck Fractures Initiates in the Superolateral Cortex: Evidence from High Speed Video of Simulated Fracture. Poster No. 943, 54th Annual Meeting of the Orthopaedic Research Society (2008). Each of these articles is incorporated herein by reference.

Medical treatment is available for a hip fracture, often in the form of a screw that is inserted into the femur, passing across the fracture along the longitudinal axis 50 of the femoral neck 44 at an approximately 45° angle with respect to the long axis 52 of the femoral shaft 47. However, there is a need for preventing hip fractures, and, more particularly, for preventing fractures along and in the region near the junction between the femoral neck 44 and the greater trochanter 46. That being said, there is a common fear that putting a metal (e.g., titanium) implant in an otherwise normal (i.e., not fractured) femur to prevent hip fractures will result in bone loss around the implant due to the relative unloading of the bone from the load-sharing nature of the stiffer metal. This phenomenon is commonly referred to as "stress shielding."

Stress shielding refers to a reduction in bone density (osteopenia) as a result of removal of normal stress from the bone by an implant (for instance, the femoral component of a hip prosthesis). According to Wolff's Law, osteopenia occurs because a bone in a healthy person or animal will remodel in response to the loads it is placed under. Therefore, if the loading on a bone decreases, the bone will become less dense and weaker because there is no stimulus for continued remodeling that is required to maintain bone mass.

Related to the concept of stress shielding is the phenomenon that the skeleton is a self-optimizing structure. Bone material in highly stressed or strained regions is preserved while bone in the low stress and strain regions is diminished by the natural remodeling process. In the hip, the bone in the inferior region of the femoral neck, otherwise referred to as the calcar region, is very dense due to the constant state of high stress and strain due to the load produced by standing and walking. Conversely, the bone in the superior region of the femoral neck, and, in particular, in the region near the junction of the superior femoral neck and the greater trochanter, becomes increasingly less dense over time due to the lack of direct loading during walking, standing, and other activities of daily living. Thus, the bone region that is the subject of greatest interest in the present application is continually being diminished in quality by the natural processes of bone remodeling. The normal bone remodeling process continually removes bone from the region of the superior femoral neck because standing, walking, or other daily activity does not generate high loads in this area. The normal load-bearing vector due to walking or other normal daily activity passes from the superior surface of the femoral head through the head to the calcar region of the proximal medial femoral shaft cortex, which is shown as the normal load-bearing vector 48 in FIG. 1. It is for this reason that natural or pharmacologic methods to augment the strength of bone often show poor results in preventing hip fractures as opposed to other fractures in other regions of the body.

Thus, there remains a need for a device and method to prevent hip fractures along and in the region near the femoral neck without causing stress shielding.

SUMMARY OF THE INVENTION

The present invention is a device and method to prevent hip fractures, and, more particularly, a device and method for preventing fractures along and in the region near the femoral neck without causing stress shielding.

An exemplary device to prevent hip fractures in accordance with the present invention includes a shaft having a first end positioned in the femoral head and the second end positioned in the greater trochanter. The device is generally inserted through the lateral prominence of the greater trochanter of the femur along a generally horizontal axis that is substantially perpendicular to the long axis of the femoral shaft. The device further includes an expanding means for engaging the femoral head at the first end. As such, the device acts as a load-bearing (or load-sharing) device along or near the line of loading resulting from a fall to the side in which impact with the ground occurs over the greater trochanter of the lateral femur. In other words, the device interacts with and distributes the load occurring within the bone, such that the device shares the load occurring during a fall, thus preventing fracture.

Another exemplary device to prevent hip fractures in accordance with the present invention includes: a screw; a tubular structure defining a screw-receiving channel and having a first end and a second end; and an expanding means for engaging the femoral head comprising a plurality of expandable fluted portions near the first end of the tubular structure. This exemplary device further includes a plurality of expandable fluted portions near the second, opposite end of the tubular structure. The tubular structure with the screw is positioned in a hole of a predetermined depth in a femur. A driving tool, such as mallet or slide hammer, is then used to drive or advance the device into the femoral head beyond the distal end of the hole to a final position, while causing the fluted portions at the first end of the tubular structure to expand and flare outward into the surrounding bone into a deployed position. As a result of expansion of the fluted portions into the surrounding bone, there is an enlarged bearing face at the first end that engages the surrounding bone. Finally, in this exemplary embodiment, once the fluted portions at the first end are in the deployed position, the screw is rotated relative to the screw-receiving channel to advance the screw, which forces the fluted portions near the second end of the tubular structure to expand outward into the surrounding bone.

Another exemplary device to prevent hip fractures in accordance with the present invention includes: a screw; a tubular structure defining a screw-receiving channel and having a first end and a second end; and an expanding means for engaging the femoral head that comprises a plurality of expanding molly bolt-like portions located near a first end. The screw has a threaded portion, and the screw-receiving channel includes corresponding and mating threads. Thus, the screw can be inserted into the tubular structure and received in the screw-receiving channel. When the device is inserted into a hole of a predetermined depth in a femur, the screw can be rotated such that the first end of the device is drawn toward the second end, effectively collapsing and forcing the plurality of molly bolt-like portions outward and into the surrounding bone.

Another exemplary device to prevent hip fractures in accordance with the present invention includes a first assembly having a first screw; a first tubular structure defining a screw-receiving channel and having a first end and a second end; and a first means for engaging the femoral head that comprises a plurality of expanding molly bolt-like portions located near the first end of the first tubular structure. Thus, the first screw can be inserted into the first tubular structure and received in the screw-receiving channel. When the device is inserted into a hole of a predetermined depth in a femur, the first screw can be rotated such that the first end of the device is drawn toward the second end, effectively collapsing and forcing the plurality of molly bolt-like portions outward and into the surrounding bone. In this exemplary embodiment, the device also includes a second assembly. The second assembly includes a second screw; a second tubular structure defining a second screw-receiving channel and having a first end and a second end; a second means for engaging the femoral head that comprises a plurality of fluted portions located near the first end of the second tubular structure; and a screw-receiving member that is positioned at the first end of the second tubular structure and has mating threads that engage the threaded portion of the second screw. The first assembly is positioned in a hole of a predetermined depth in a femur, and the plurality of molly bolt-like portions are forced outward and into the surrounding bone. The first screw is then removed, while the first tubular structure remains in the femur. The entire second assembly is then advanced through the first tubular structure until its first end is in proximity to the expanded molly bolt-like portions of the first assembly. The fluted portions of the second assembly are then expanded by rotating the second screw, which draws the screw-receiving member toward the second end and forces the fluted portions to expand outward into the surrounding bone.

Another exemplary device in accordance with the present invention includes a main shaft; a plurality of rods surrounding the main shaft; a first end cap located at a first end of the device; a plurality of links, each connecting one of the rods to the first end cap; and a sleeve for maintaining the positioning of the rods relative to the main shaft. Each link is pivotally connected to the first end cap at one end about a pivot axis, and each defines a cavity near its opposite end for receiving the distal end of one of the rods. When the device is inserted into the hole, each of the rods is individually advanced towards the first end to cause a controlled flaring of the rod into the surrounding bone. In turn, each of the rods is similarly advanced such that all of the rods and links are expanded outward and away from the main shaft into a deployed position.

Another exemplary device in accordance with the present invention includes a main shaft; a plurality of rods surrounding the main shaft; a first end cap located at a first end of the device and having a flared circumferential surface; and a sleeve for maintaining the positioning of the rods relative to the main shaft. When the device is inserted into the hole, each of the rods is individually advanced towards the first end. As each rod is advanced, its distal end contacts the flared circumferential surface of the first end cap, which forces the rod outward into the surrounding bone. In turn, each of the rods is similarly advanced such that all of the rods are flared outward and away from the main shaft, resulting into a deployed position.

DESCRIPTION OF THE DRAWINGS

FIG. 28 is a side view of another exemplary device to prevent hip fractures made in accordance with the present invention;

FIG. 29 is a side view of the device of FIG. 28, illustrating the rods at the first end in a deployed position;

DETAILED DESCRIPTION OF THE INVENTION

The present invention is a device and method to prevent hip fractures, and, more particularly, a device and method for preventing fractures along and in the region near the femoral neck without causing stress shielding.

An exemplary device to prevent hip fractures made in accordance with the present invention includes a shaft having a first end positioned in the femoral head and the second end positioned in the greater trochanter. The device is generally inserted through the lateral prominence of the greater trochanter of the femur generally along a horizontal axis 54 that is substantially perpendicular to the long axis 52 of the femoral shaft 47. The device further includes an expanding means for engaging the femoral head 42 at the first end, as will be further discussed below. As such, the device acts as a load-bearing (or load-sharing) device along or near the line of loading resulting from a fall to the side in which impact with the ground occurs over the greater trochanter of the lateral femur, as will be further discussed below.

Furthermore, because of the orientation of this device within the femur, it will protect the bone in the superior region of the femoral neck where it is believed that a fracture due to a fall to the side initiates as a compression or buckling fracture. This bone is buttressed by the presence of the device. Also, as a result of the positioning of the device within the femur, along with the means for engaging the femoral head 42 that is provided at the first end of the device, the risk that the device will penetrate through the femoral head to the articular surface of the hip joint is minimized. Furthermore, the presence of the device should not compromise the health of the bone underlying the joint surface or lead to a condition such as avascular necrosis. Placing too much foreign material (e.g., metal, cement, etc) in the subchondral bone can reduce blood supply and nutrition to the load-bearing bone of the femoral head 42.

Figure 6:
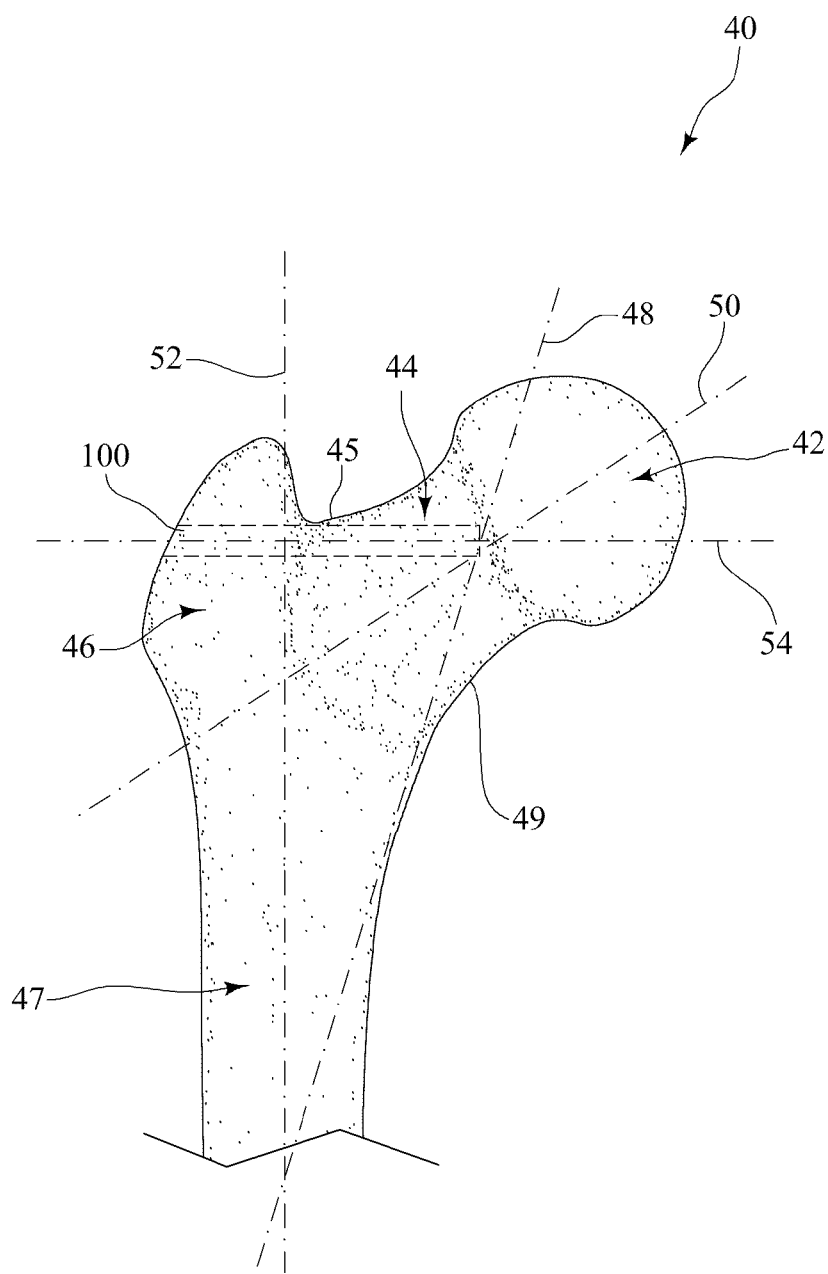
FIG. 6 is a front view of a portion of the femur, illustrating a hole formed along a generally horizontal axis that is substantially perpendicular to the long axis of the femoral shaft.

Referring initially to FIG. 6, a hole 100 of a predetermined depth is formed along a generally horizontal axis 54 that is substantially perpendicular to the long axis 52 of a femoral shaft 47 of the femur 40. Any known method for forming the hole 100 may be used. For example, one method may include drilling to a predetermined depth with a sufficient cross-sectional area to accommodate insertion of the device. Alternatively, it may be preferable to drill a small pilot hole to the predetermined depth and then dilate and compact the cancellous (lattice-like or spongy structured) bone of the femur to create a hole of a sufficient cross-section area to accommodate insertion of the device. In any event, in some exemplary embodiments, and as shown in FIG. 6, the hole 100 terminates at or near the axis 48 of the normal load-bearing vector. Of course, it is also preferred that the device be inserted through a minimally invasive approach through as small a hole as possible.

FIGS. 7-11 illustrate another exemplary device 10 to prevent hip fractures made in accordance with the present invention. This exemplary device 10 includes: a screw 12; a tubular structure 14 defining a screw-receiving channel 16 and having a first end 18 and a second end 20; and an expanding means for engaging the femoral head 42 comprising a plurality of expandable fluted portions 22 near the first end 18 of the tubular structure 14. This exemplary device further includes a plurality of expandable molly bolt-like portions 24 near the second, opposite end 20 of the tubular structure 14. In other words, the screw 12 and the tubular structure 14 serve as the "shaft" of the device, while the "ends" are in the form of the expandable fluted portions 22 and the expandable molly bolt-like portions 24 at either end 18, 20 of the tubular structure 14. The screw-receiving channel 16 is accessible through the second end 20 of the tubular structure 14.

Figure 8:
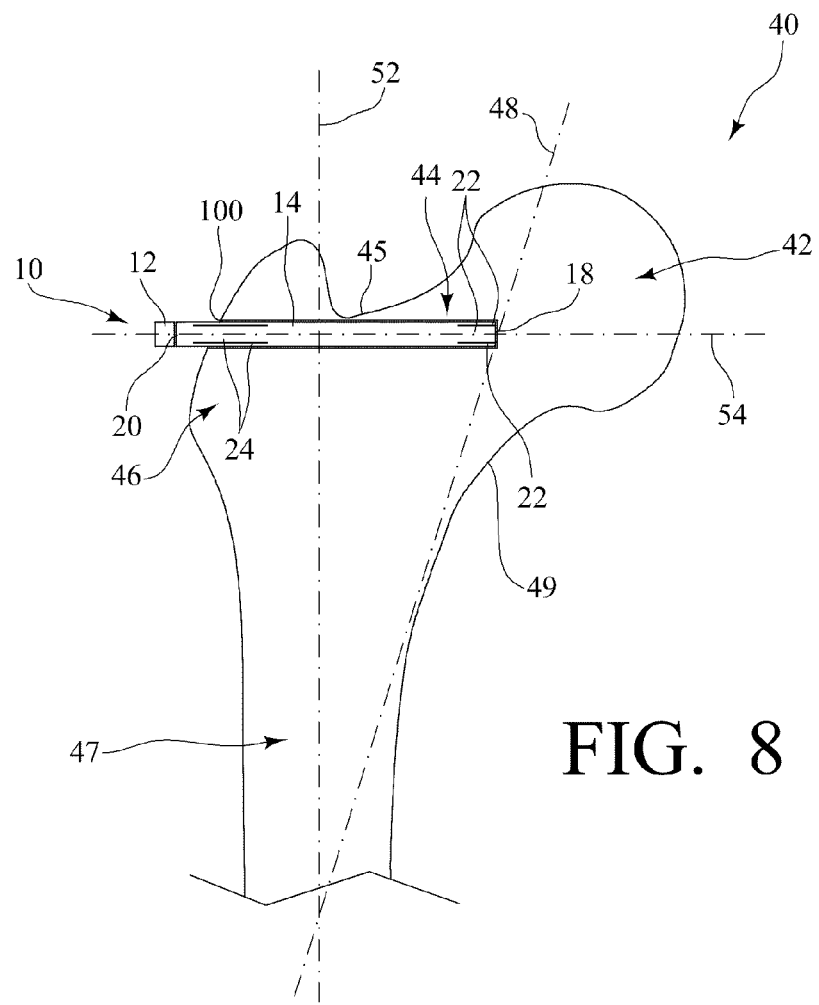
FIG. 8 is a view of the device of FIG. 7 that illustrates its placement into the hole formed along the generally horizontal axis that is substantially perpendicular to the long axis of the femoral shaft.
Figure 9:
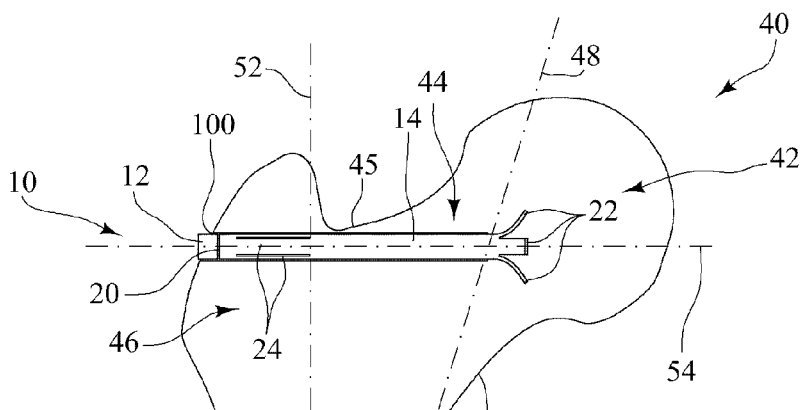
FIG. 9 is a view of the device of FIG. 7 that illustrates the fluted portions at the first end in a deployed position.

The screw 12 has a threaded portion 12a, and the screw-receiving channel 16 includes corresponding and mating threads 16a. Thus, the screw 12 can be inserted into the tubular structure 14 and received in the screw-receiving channel 16. The tubular structure 14 with the screw 12 is positioned in a hole 100 of a predetermined depth in a femur 40, as best shown in FIG. 8. Then, a driving tool (such as a mallet or slide hammer) is used to drive or advance the device 10 into the femoral head 42 beyond the distal end of the hole 100 to a final predetermined depth and position, while causing the fluted portions 22 at the first end 18 of the tubular structure 14 to expand and flare outward into the surrounding bone into a deployed position, as best shown in FIG. 9. As a result of expansion of the fluted portions 22 into the surrounding bone, there is an enlarged bearing face at the first end that engages the surrounding bone, as perhaps best illustrated in the end view of FIG. 11. This enlarged bearing face aids in ensuring that the position of the device 10 remains fixed within the femur.

Figure 11:
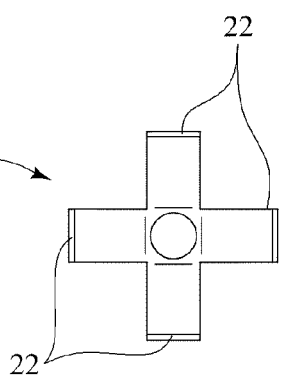
FIG. 11 is an end view of the device of FIG. 7, illustrating the fluted portions at the first end in a deployed position.
Figure 10:
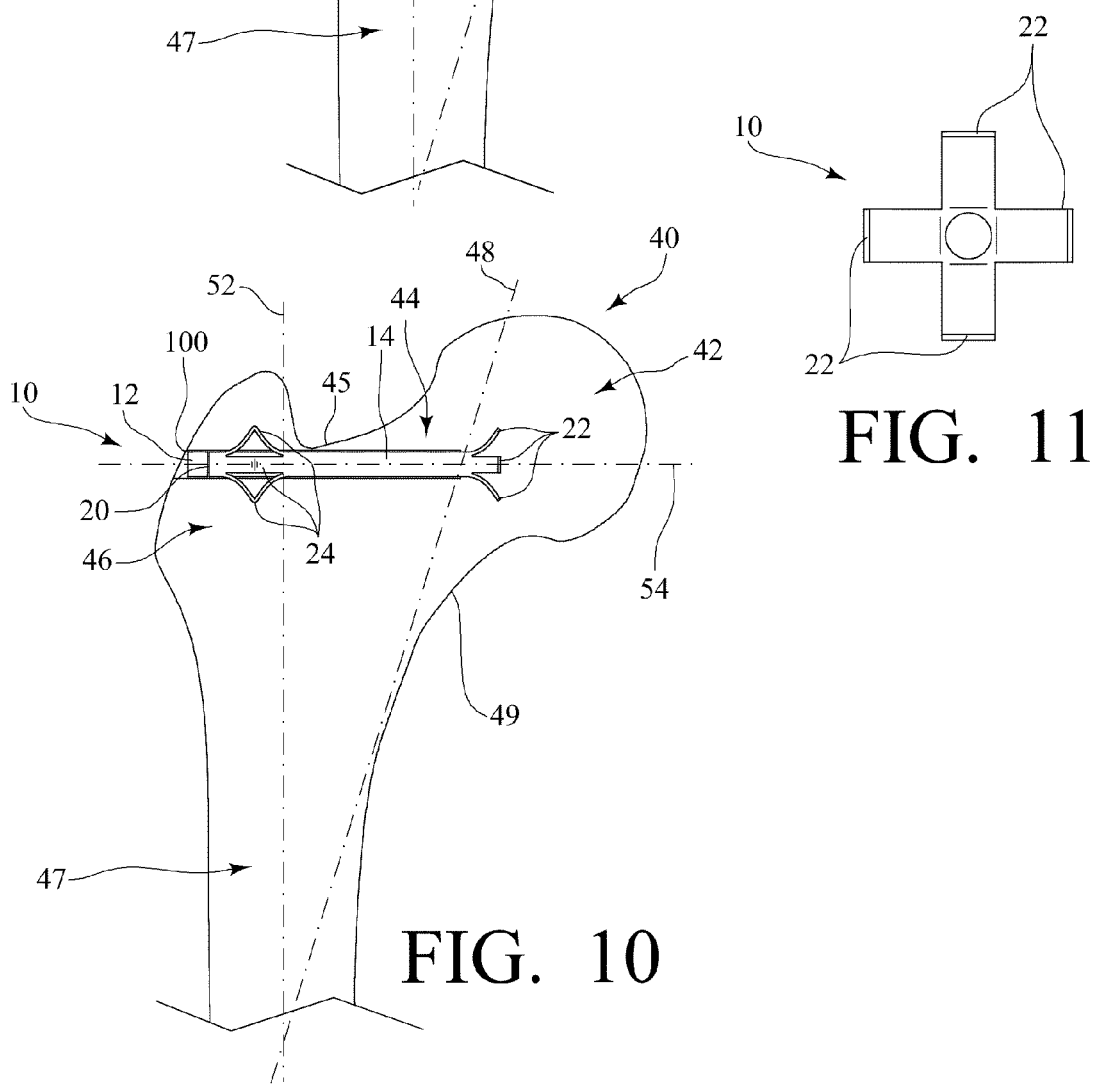
FIG. 10 is a view of the device of FIG. 7 that illustrates the fluted portions at the first end in a deployed position and the molly bolt-like portions at the second end in a deployed position.

Finally, once the fluted portions 22 at the first end 18 are in the deployed position, the screw 12 is rotated relative to the screw-receiving channel 16a to advance the screw 12, which forces the molly bolt-like portions 24 near the second end 20 of the tubular structure 14 to expand outward into the surrounding bone, as shown in FIGS. 10 and 11. Specifically, in this exemplary embodiment, molly bolt-like portions near the second end 20 of the tubular structure 14 are integral with and form the side wall of the tubular structure 14, and as the screw 12 is rotated, the head of the screw 12 engages and presses against the second end 20 of the tubular structure 14, effectively applying a compressive load that causes the molly bolt-like portions 24 to collapse and flare outward into the surrounding bone to fix the position of the device within the femur 40.

Figure 1:
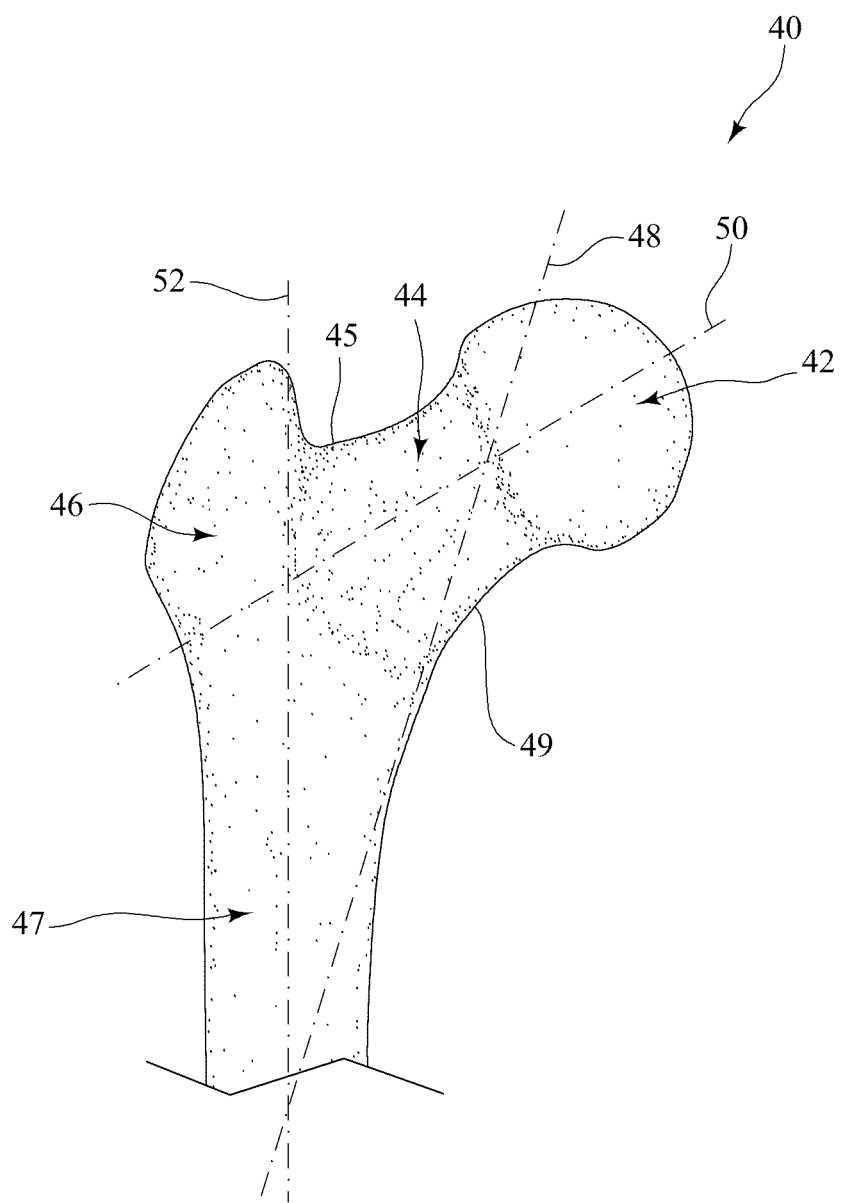
FIG. 1 is a front view of the upper portion of a femur.
Figure 2:
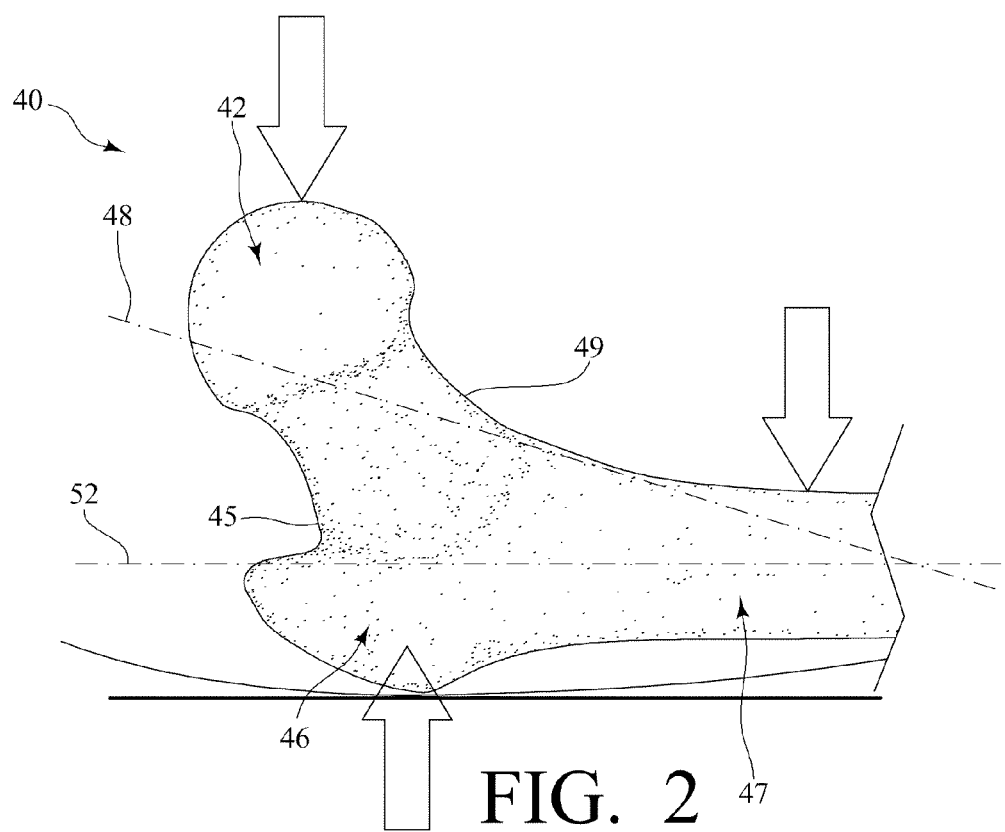
FIG. 2 is a front view of a portion of the femur, illustrating the loads applied to the femur as a result of the impact from a fall to the side.
Figure 3:
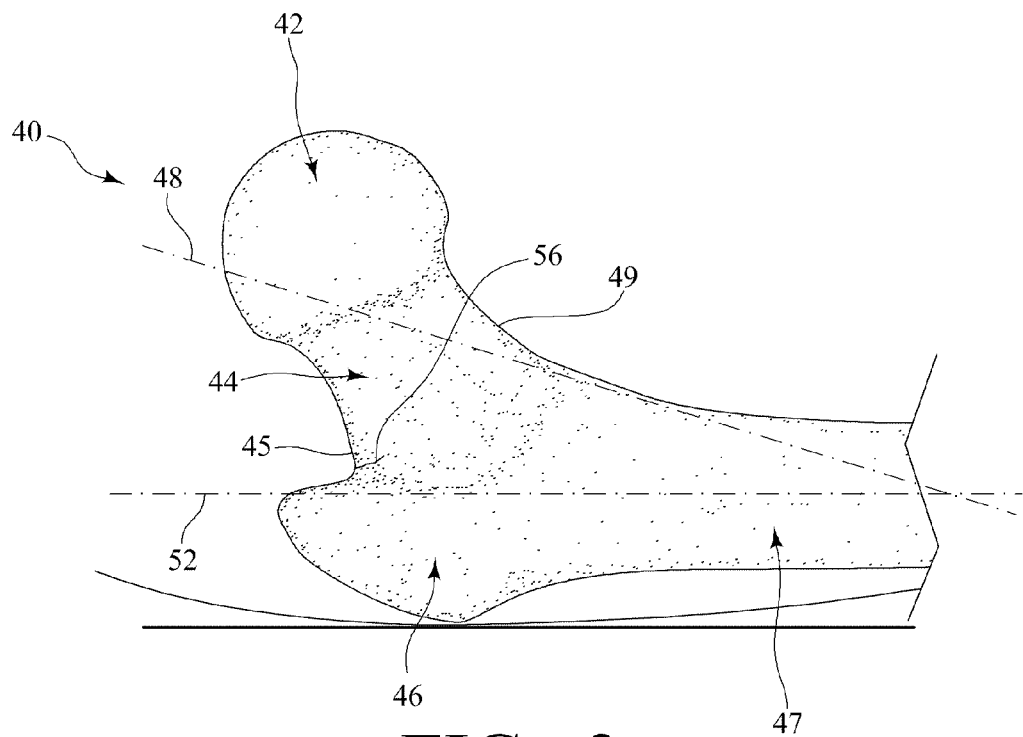
FIG. 3 is a front view of a portion of the femur, illustrating a crack around the superior region of the femoral neck.
Figure 4:
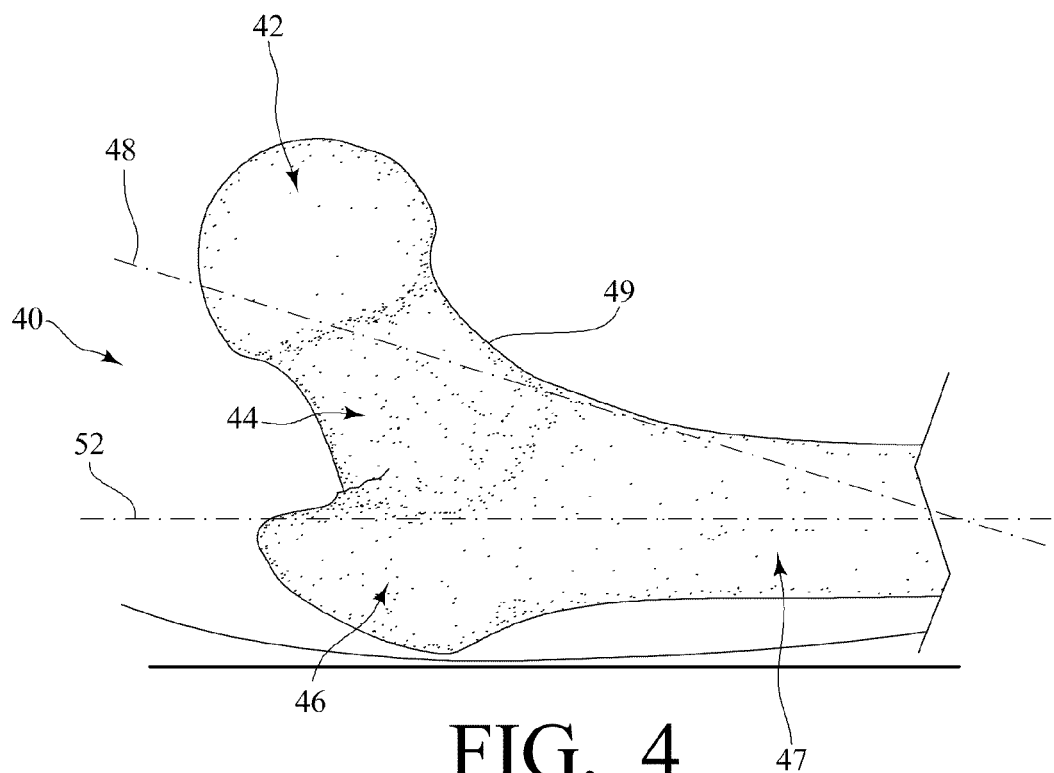
FIG. 4 is a front view of a portion of the femur, illustrating the crack propagating.
Figure 5:
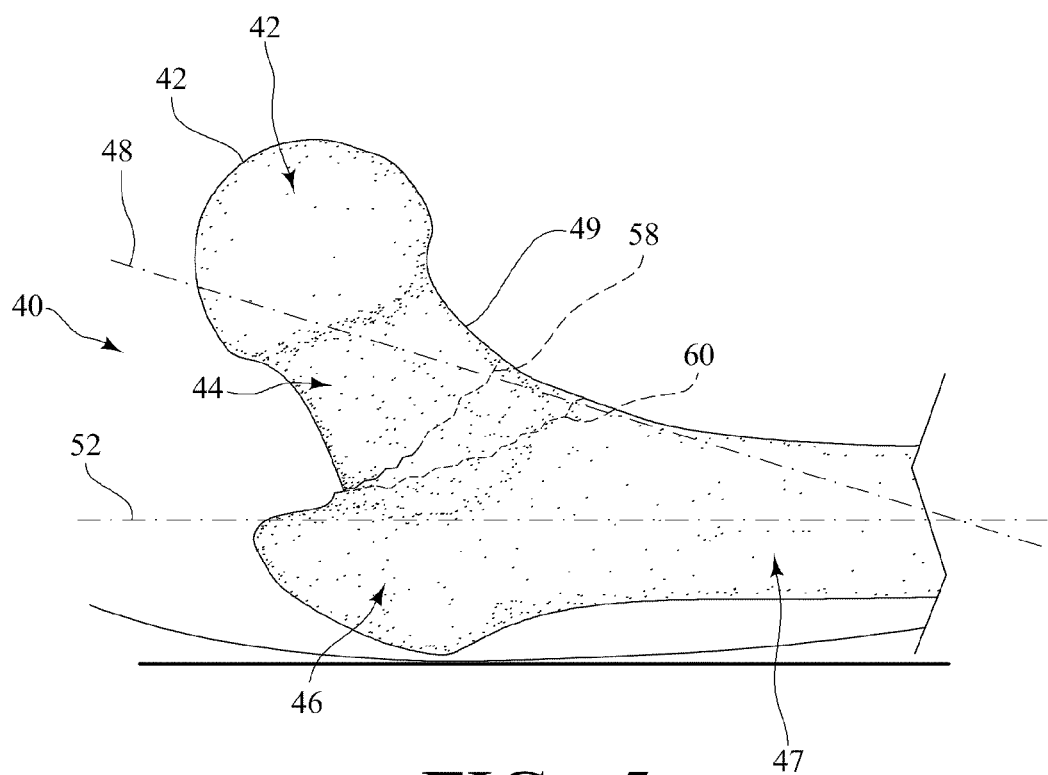
FIG. 5 is a front view of a portion of the femur, illustrating the crack propagating into a femoral neck fracture or an intertrochanteric fracture.

Referring back to FIG. 5, by implanting the device 10 through and along the upper side of the neck of the femur 40 in line with a load that would be generated during a fall to the side with an impact to the greater trochanter 46, the device 10 acts as a load-bearing (or load-sharing) device along or near the line of loading 54 resulting from a fall to the side, sharing the compressive load developed along this line during a fall. When the load-bearing or load-sharing is sufficient, the initial compressive failure in the bone substance at the junction of the superior region of the femoral neck 44 and the greater trochanter 46 can be prevented, thus preventing the hip fracture. Also, the enlarged bearing faces at the ends 18, 20 of the device 10 that results from the expansion of the fluted portions 22 and the molly bolt-like portions 24 causes a greater percentage of the load to pass through the device 10 instead of the surrounding bone, thus improving the ability of the device 10 to stiffen and strengthen the load pathway through the femur.

With respect to the size of the device, data indicates that the average breaking force for femurs loaded in a fall-to-the-side configuration is approximately 2800 N for the at-risk group (e.g., older females). See Pulkkinen et al. Association of Geometric Factors and Failure Load Level With the Distribution of Cervical vs. Trochanteric Hip Fractures. *Journal of Bone and Mineral Research*, Vol. 21, No. 6, 2006. This article is incorporated herein by reference. Thus, it is desired that the device of the present invention be capable of load-bearing or load-sharing approximately 2500 N without allowing significant displacement of the device in the loading direction, i.e., less than 2 mm.

Preliminary test data using devices loaded against poor quality cancellous bone-simulating foam and against real cancellous bone specimens have shown that the effective cross-sectional area of the bearing face (i.e., the interface between the device and the bone in the device axis/load direction) should be approximately 500 $mm^2$ or more. For example, a bearing a 25-mm diameter will suffice in cancellous bone with a strength of 5 MPa.

Lastly, it should be noted that, although four fluted portions 22 and four molly bolt-like portions 24 are located at the ends 18, 20 of the device 10 in this exemplary embodiment, any other suitable number could be used without departing from the spirit or scope of the present invention.

Figure 7:
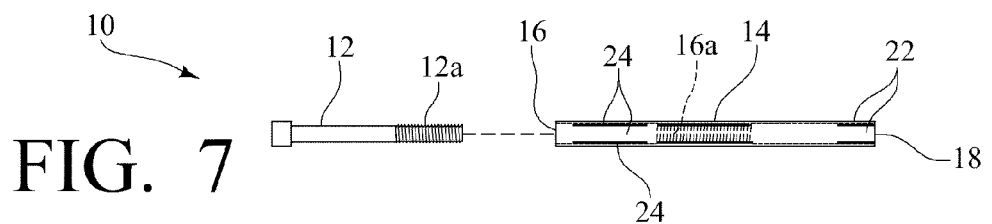
FIG. 7 is an exploded side view of an exemplary device to prevent hip fractures made in accordance with the present invention.
Figure 7A:
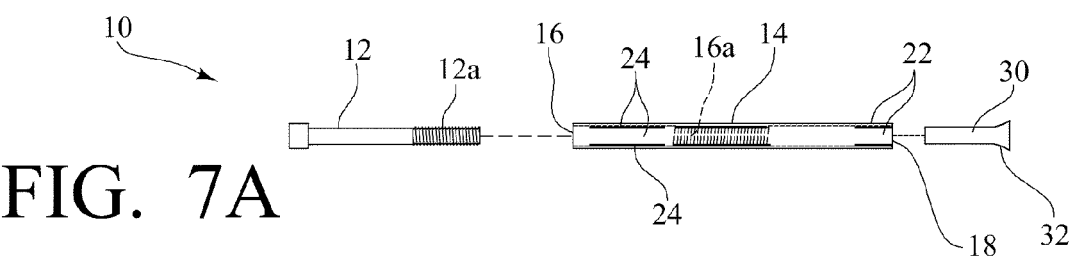
FIG. 7A is an exploded side view of an exemplary device to prevent hip fractures similar to FIG. 7, but further including an end cap.

FIG. 7A is an exploded side view of an exemplary device to prevent hip fractures similar to FIG. 7, but further including an end cap 30 at the first end 18 of the tubular structure 14. This end cap 30 would be held in place (for example, by a line passing through the center of the tubular structure 14) while the device 10 is driven and advanced beyond the distal end the hole 100, such that the flared circumferential surface 32 of the end cap 30 would assist the fluted portions 22 in expanding and flaring outward into the surrounding bone.

Figure 12:
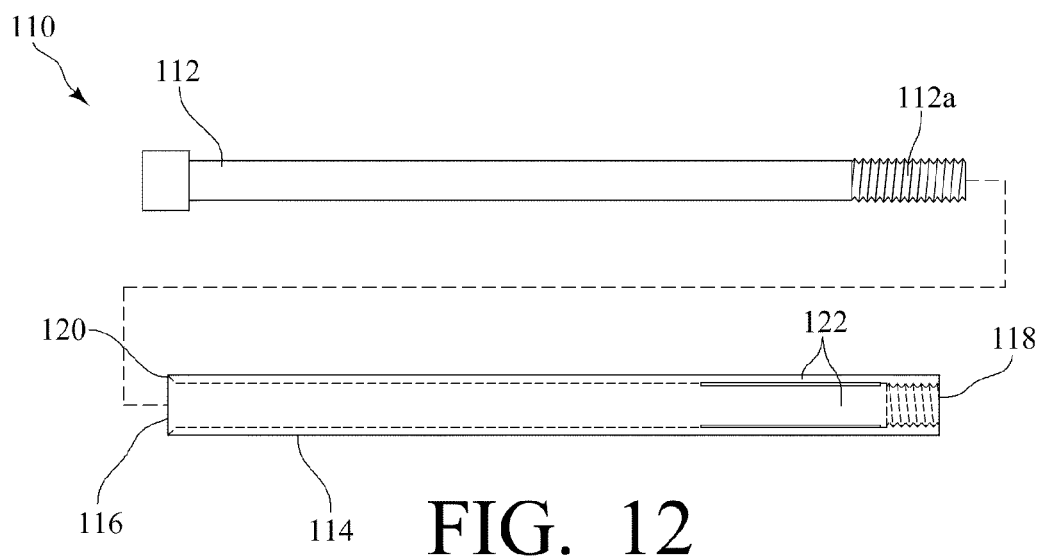
FIG. 12 is an exploded side view of another exemplary device to prevent hip fractures made in accordance with the present invention.
Figure 13:
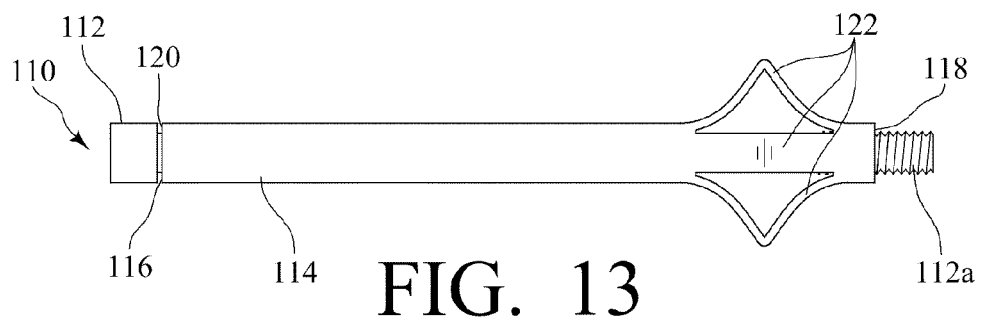
FIG. 13 is a side view of the device of FIG. 12, illustrating the molly bolt-like portions in a deployed position.
Figure 14:
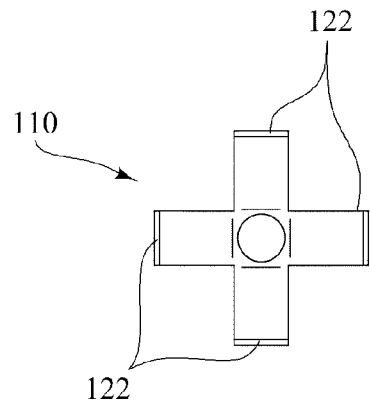
FIG. 14 is an end view of the device of FIG. 12, illustrating the molly bolt-like portions in a deployed position.
Figure 15:
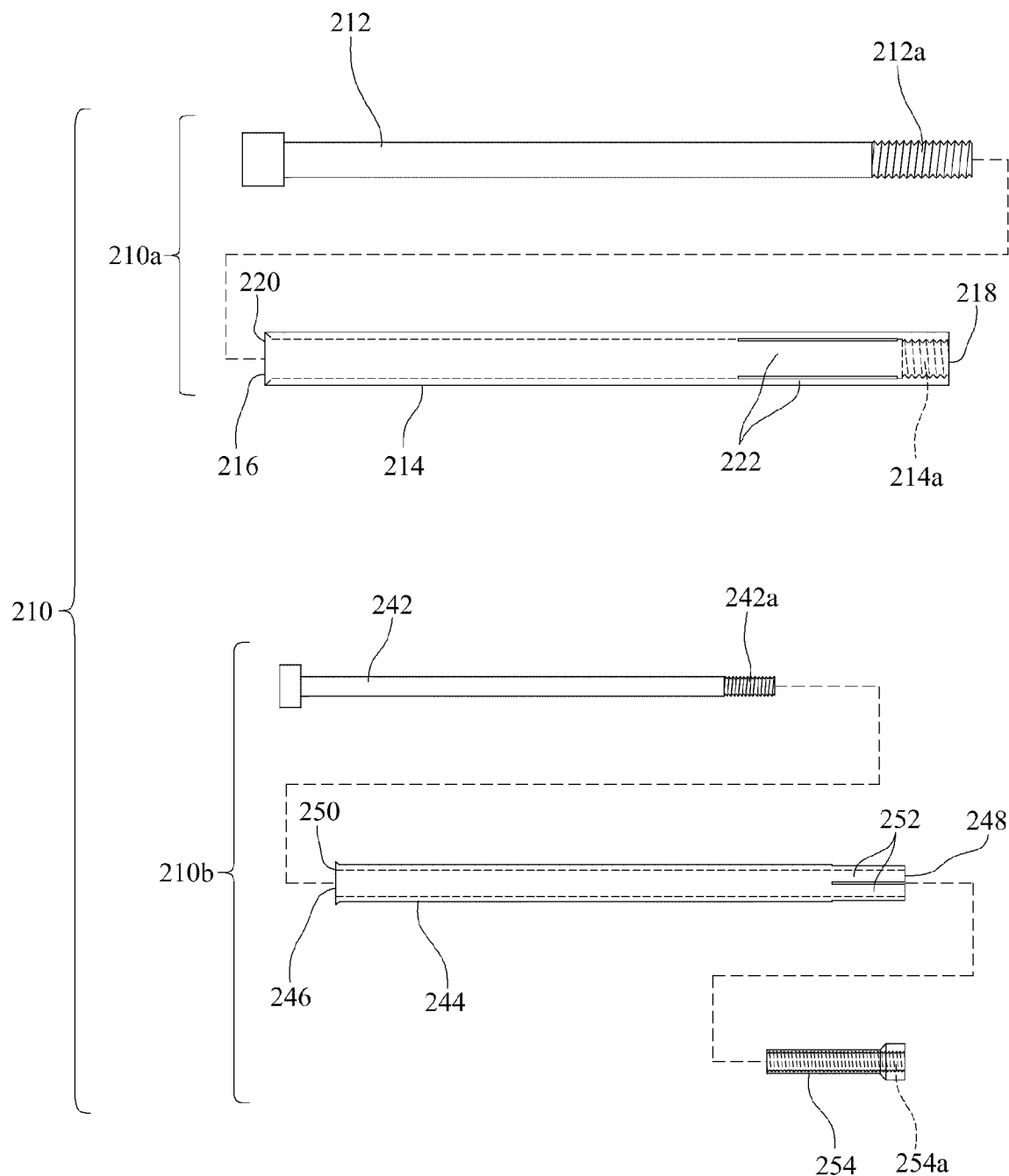
FIG. 15 is an exploded side view of another exemplary device to prevent hip fractures made in accordance with the present invention.

FIGS. 12-14 illustrate another exemplary device 110 to prevent hip fractures made in accordance with the present invention. This exemplary device 110 includes: a screw 112; a tubular structure 114 defining a screw-receiving channel 116 and having a first end 118 and a second end 120; and an expanding means for engaging the femoral head 42 that comprises a plurality of expanding molly bolt-like portions 122 located near a first end 118. The screw 112 has a threaded portion 112a, and the screw-receiving channel 116 includes corresponding and mating threads 116a. Thus, the screw 112 can be inserted into the tubular structure 114 and received in the screw-receiving channel 116. When the device 110 is inserted into the hole 100 (as shown in FIG. 6), the screw 112 can be rotated such that the first end 118 of the device is drawn toward the second end 120, effectively collapsing and forcing the plurality of molly bolt-like portions 122 outward and into the surrounding bone. As with the embodiment described above with respect to FIGS. 7-11, the expansion of the plurality of molly bolt-like portions 122 into the surrounding bone creates an enlarged bearing face, as illustrated in the end view of FIG. 14, that contacts and engages the surrounding bone, thus fixing the position of the device 110 within the femur.

It should be noted that although four molly bolt-like portions 122 are located at the first end 118 of the device 110 in this exemplary embodiment, any other suitable number could be used without departing from the spirit or scope of the present invention.

Figure 16:
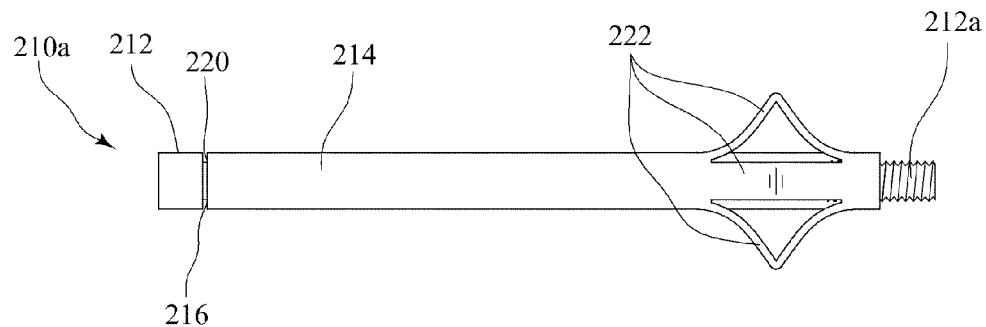
FIG. 16 is a side view of the device of FIG. 15, illustrating the molly bolt-like portions of the device in a deployed position.
Figure 17:
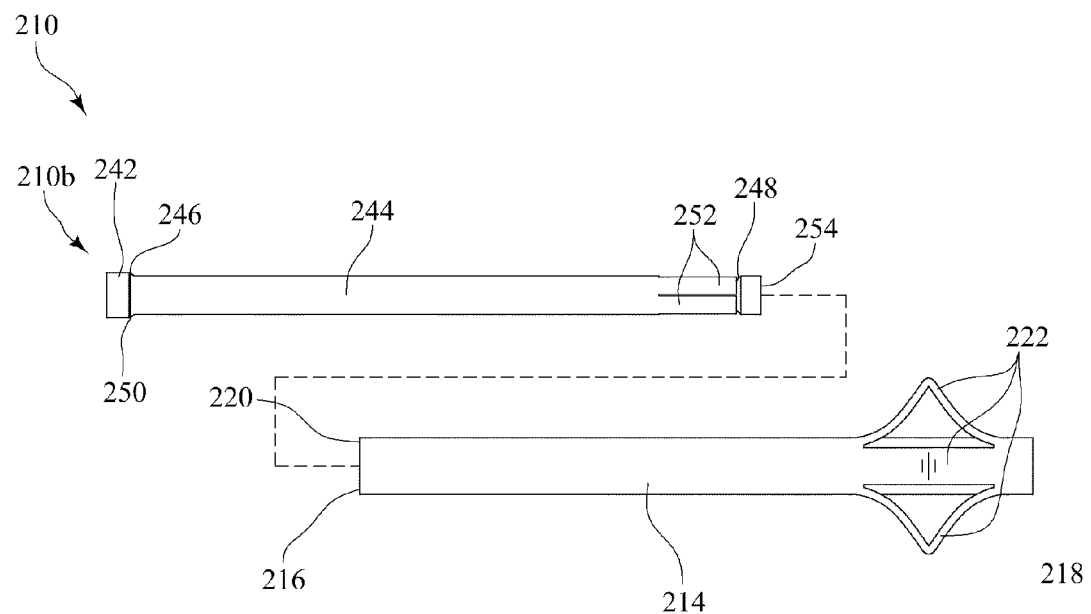
FIG. 17 is an exploded side view of the device of FIG. 15, illustrating the advancement of the second assembly of the device into the first assembly.
Figure 18:
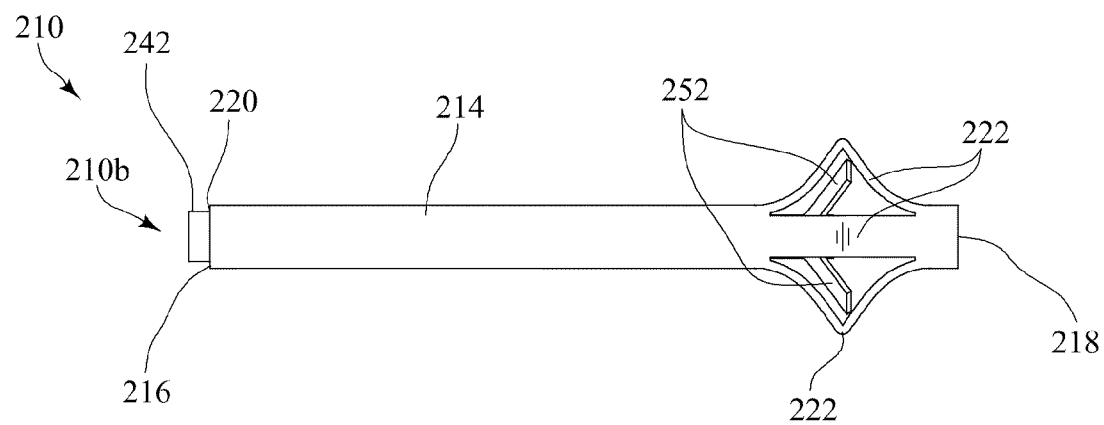
FIG. 18 is a side view of the device of FIG. 15, illustrating the fluted portions and the molly bolt-like portions of the device in a deployed position.

FIGS. 15-19 illustrate another exemplary device 210 to prevent hip fractures made in accordance with the present invention. This exemplary device 210 includes a first assembly 210a having a first screw 212; a first tubular structure 214 defining a screw-receiving channel 216 and having a first end 218 and a second end 220; and a first means for engaging the femoral head 42 that comprises a plurality of expanding molly bolt-like portions 222 located near the first end 218 of the first tubular structure 214. The first screw 212 has a threaded portion 212a, and the screw-receiving channel 216 includes corresponding and mating threads 216a. Thus, the first screw 212 can be inserted into the first tubular structure 214 and received in the screw-receiving channel 216. Like the embodiment described above with reference to FIGS. 12-14, when the device 210 is inserted into the hole 100 (as shown in FIG. 6), the first screw 212 can be rotated such that the first end 218 of the device is drawn toward the second end 220, effectively collapsing and forcing the plurality of molly bolt-like portions 222 outward and into the surrounding bone, as shown in FIG. 18.

However, unlike the embodiment described above with reference to FIGS. 12-14, in this exemplary embodiment, the device 210 includes a second assembly 210b. The second assembly 210b includes a second screw 242; a second tubular structure 244 defining a second screw-receiving channel 246 and having a first end 248 and a second end 250; a second means for engaging the femoral head 42 that comprises a plurality of fluted portions 252 located near the first end 248 of the second tubular structure 244; and a screw-receiving member 254 that is positioned at the first end 248 of the second tubular structure 244 and has mating threads 254a that engage the threaded portion 242a of the second screw 242.

Figure 19:
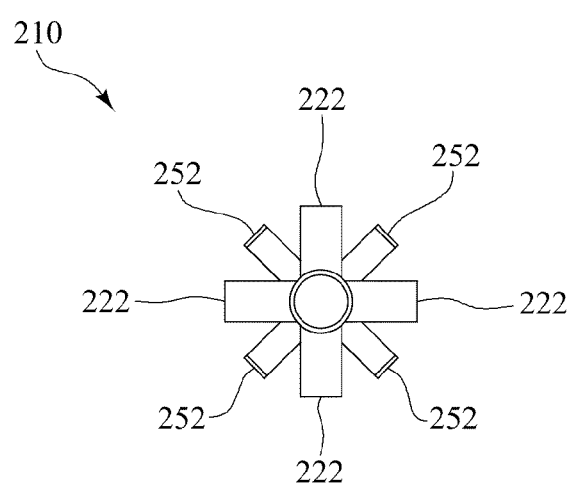
FIG. 19 is an end view of the device of FIG. 15, illustrating the fluted portions and the molly bolt-like portions of the device in a deployed position.
Figure 20:
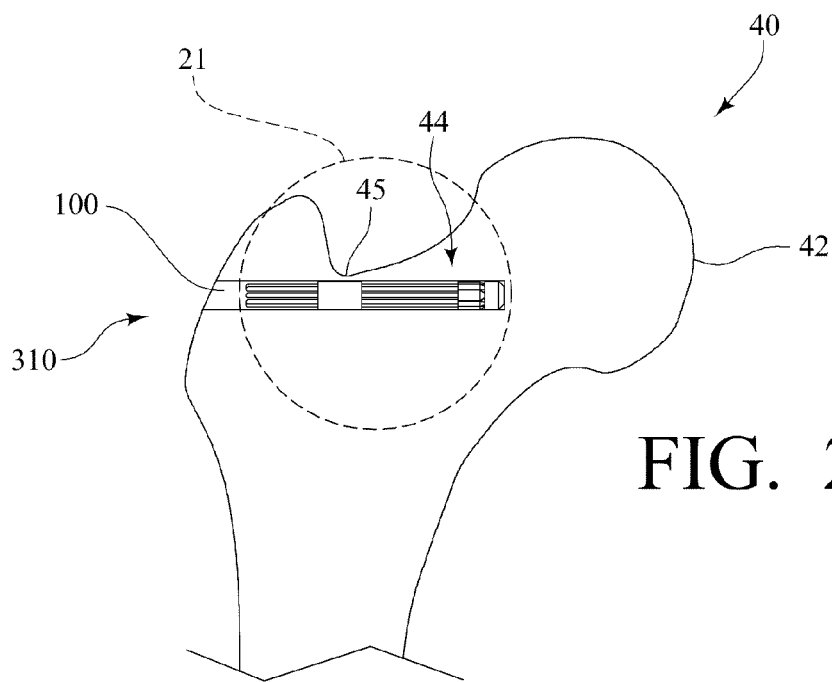
FIG. 20 is a view of another exemplary device to prevent hip fractures made in accordance with the present invention as positioned in a femur.
Figure 21:
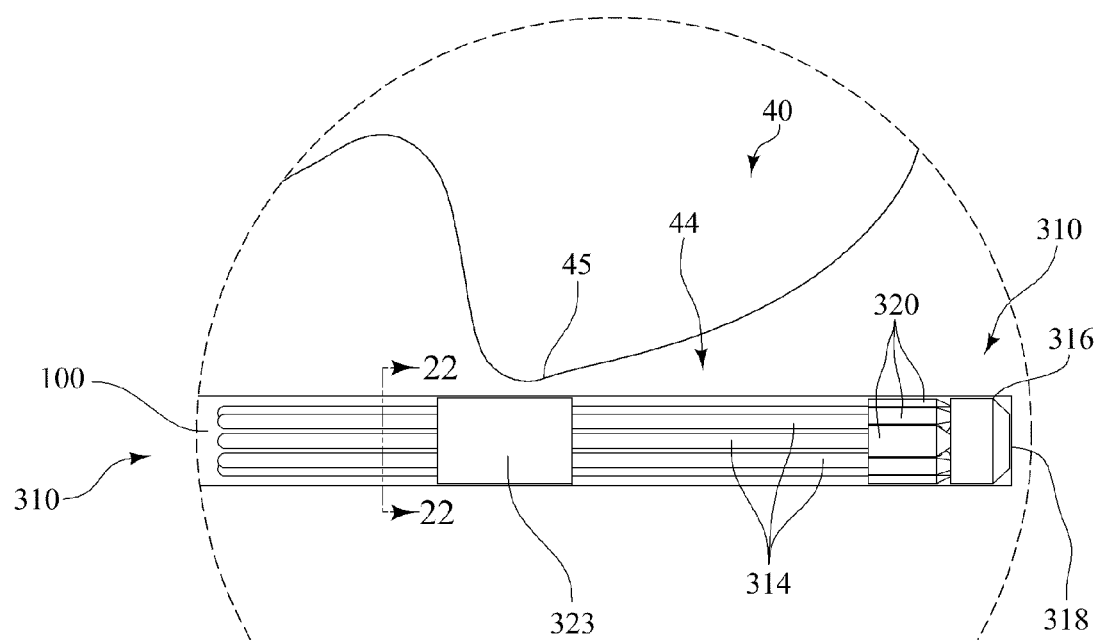
FIG. 21 is an enlarged view of the device of FIG. 20.
Figure 22:
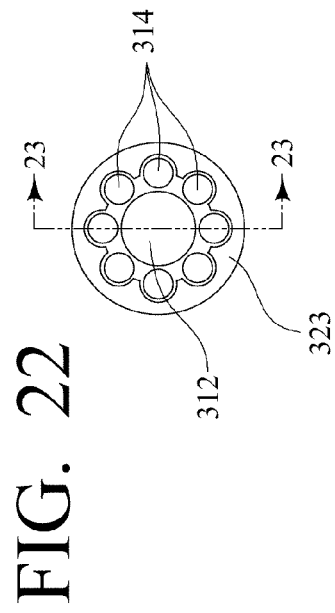
FIG. 22 is a sectional view of the device of FIG. 20 taken along line 22-22 of FIG. 20.

In practice, the first assembly 210a is positioned in the hole 100 (as shown in FIG. 6), and the plurality of molly bolt-like portions 222 is forced outward and into the surrounding bone, as shown in FIG. 16. The first screw 212 is then removed, while the first tubular structure 214 remains in the femur 40. The entire second assembly 210b is then advanced through the first tubular structure 214 until its first end 248 is in proximity to the expanded molly bolt-like portions 222 of the first assembly 210a, as shown in FIG. 17. The fluted portions 252 of the second assembly 210b are then expanded by rotating the second screw 242, which draws the screw-receiving member 254 toward the second end 250 and forces the fluted portions 252 to expand outward into the surrounding bone, as shown in FIGS. 18 and 19.

Referring now to FIGS. 20-27, another exemplary device 310 made in accordance with the present invention includes a main shaft 312; a plurality of rods 314 surrounding the main shaft 312; a first end cap 316 located at a first end 318 of the device 310; a plurality of links 320, each connecting one of the rods 314 to the first end cap 316; and a sleeve 323 for maintaining the positioning of the rods 314 relative to the main shaft 312. With respect to the links 320, each link 320 is pivotally connected to the first end cap 316 at one end about a pivot axis 322, and each defines a cavity 320a near its opposite end for receiving the distal end of one of the rods 314.

Figure 23:
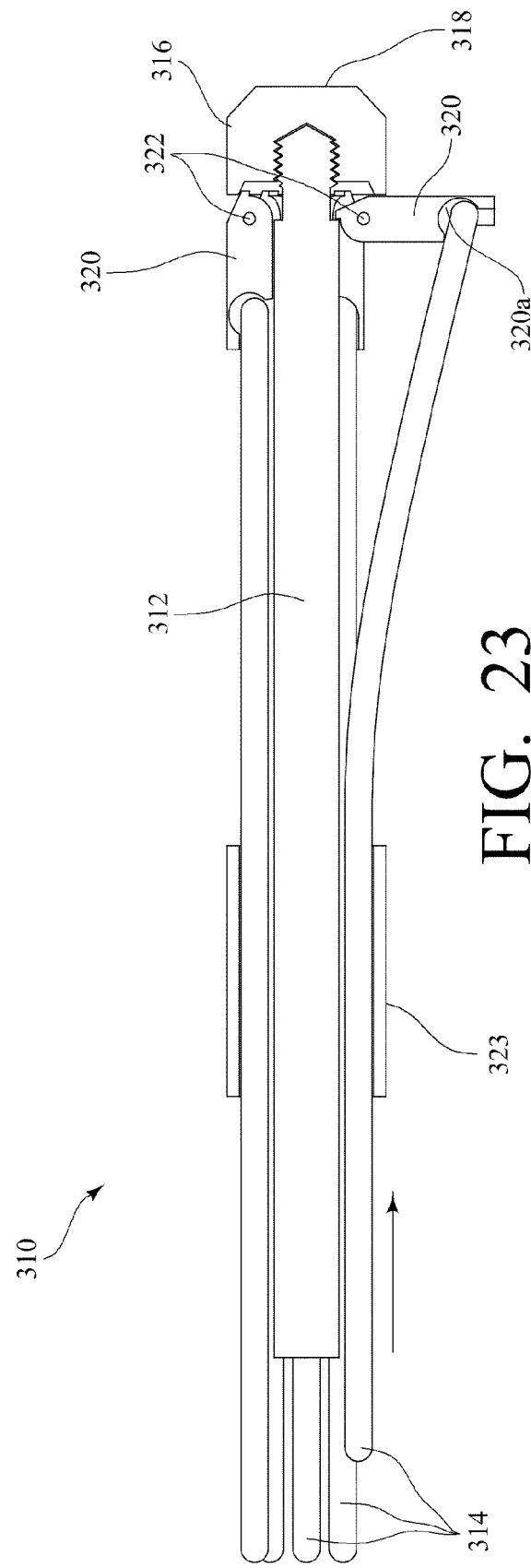
FIG. 23 is a side view of the device of FIG. 20 taken along line 23-23 of FIG. 22, and illustrating one of the rods being placed in a deployed position.
Figure 24:
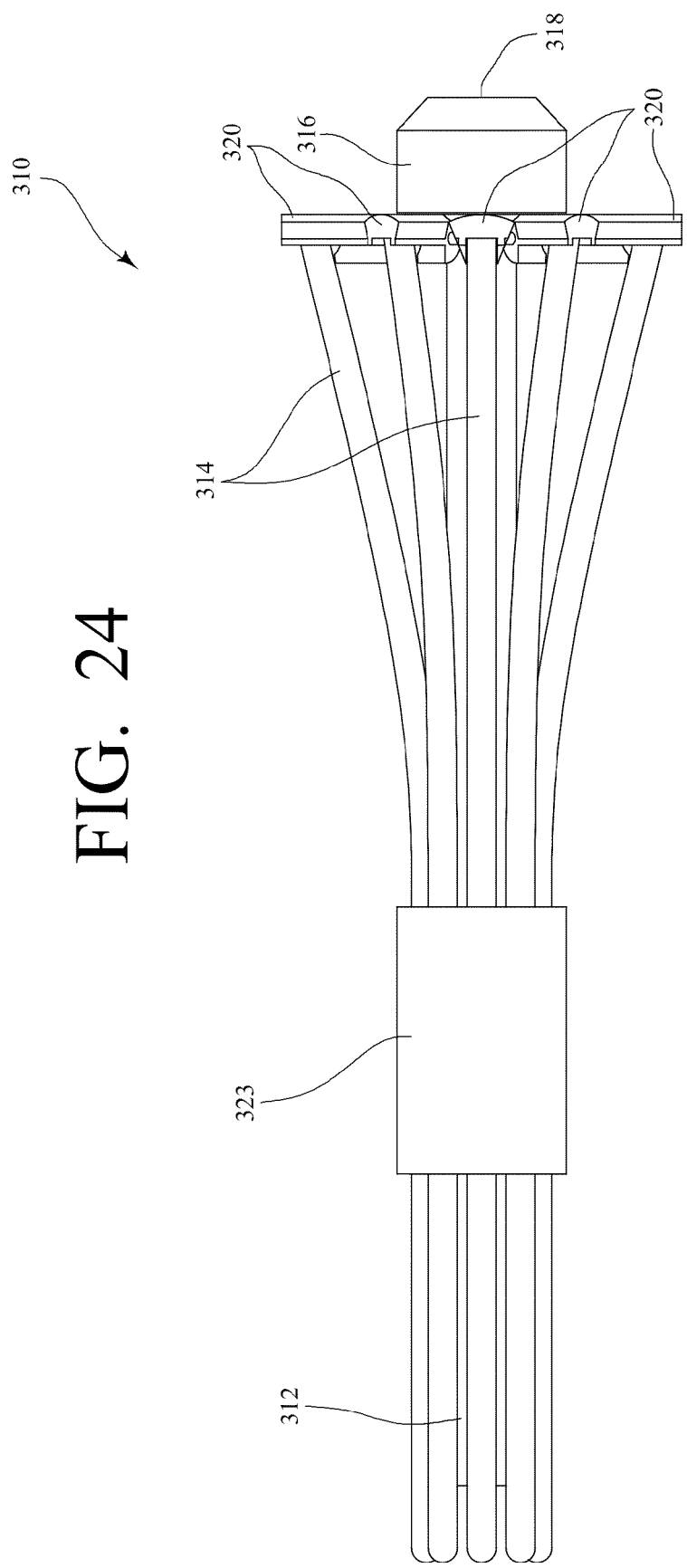
FIG. 24 is a side view of the device of FIG. 20, illustrating all of the rods in a deployed position.
Figure 25:
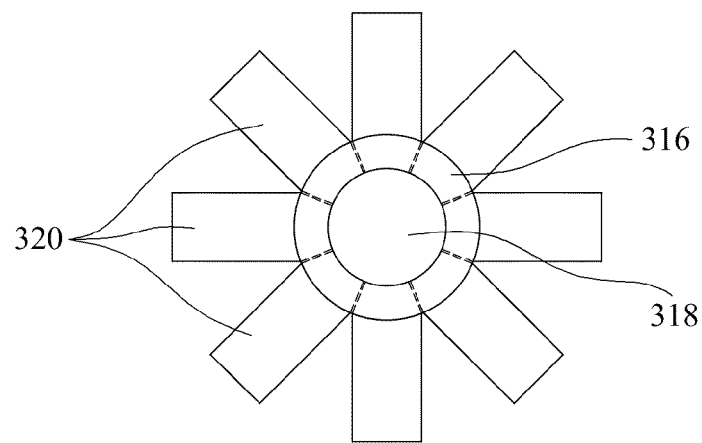
FIG. 25 is an end view of the device of FIG. 20, illustrating all of the rods in a deployed position.

When the device 310 is inserted into the hole 100 (as shown in FIG. 6), each of the rods 314 is individually advanced towards the first end 318, as shown in FIG. 23. As a result of the forward movement of each rod 314, the distal end of the rod presses into the cavity 320a defined by the link 320, causing the respective link to rotate about the respective pivot axis 322. As a result, there is a controlled flaring of the rod 314 into the surrounding bone. In turn, each of the rods 314 is similarly advanced such that all of the rods 314 and links 320 are expanded outward and away from the main shaft 312, resulting in the deployed position shown in FIGS. 24 and 25.

It should be noted that although eight rods 314 are used in this exemplary embodiment, any other suitable number could be used without departing from the spirit or scope of the present invention.

It should also be noted that, by individually advancing the rods 314 into the surrounding bone, the amount of resistance force at any time will be kept low as compared to a simultaneous advancement of all rods 314. This minimizes the possibility of forcing the device 310 past its desired position in the femur and/or any penetration through the femoral head to the articular surface of the hip joint. Furthermore, by individually advancing the rods 314 into the surrounding bone, each rod may be advanced until a predetermined resistance is achieved, resulting in rods 314 that extend to varying depths within the femoral head 42.

Figure 26:
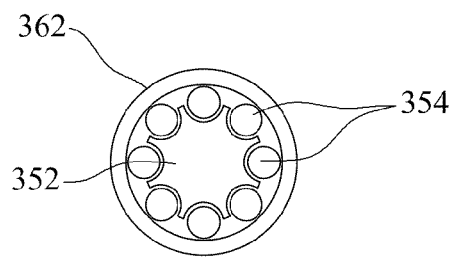
FIG. 26 is a sectional view similar to FIG. 22, but illustrating an alternative main shaft for the device of FIG. 20.

As a further refinement, and as shown in FIG. 26, an alternate main shaft 352 may be provided that defines a plurality of recesses to receive and work in conjunction with a sleeve 362 to control and guide the movement of each of the plurality of rods 354.

Figure 27:
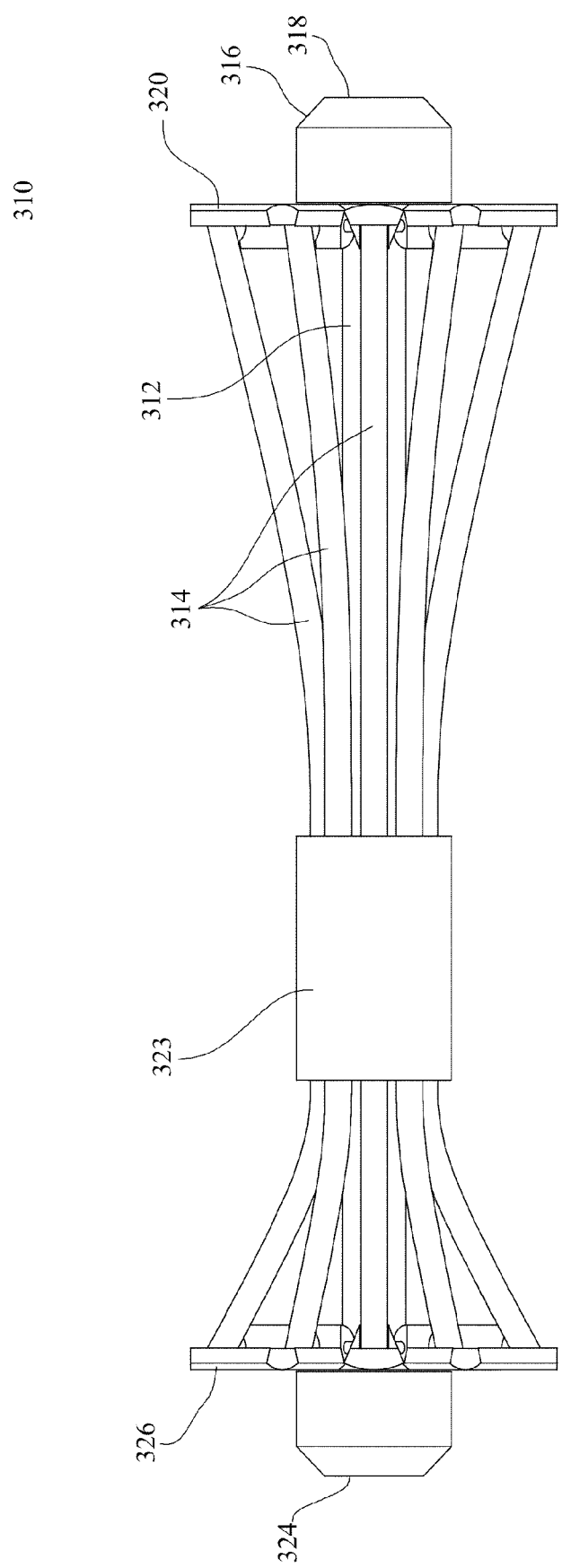
FIG. 27 is a side view of another exemplary device to prevent hip fractures made in accordance with the present invention as positioned in a femur, in which rods are deployed at both ends.
Figure 30:
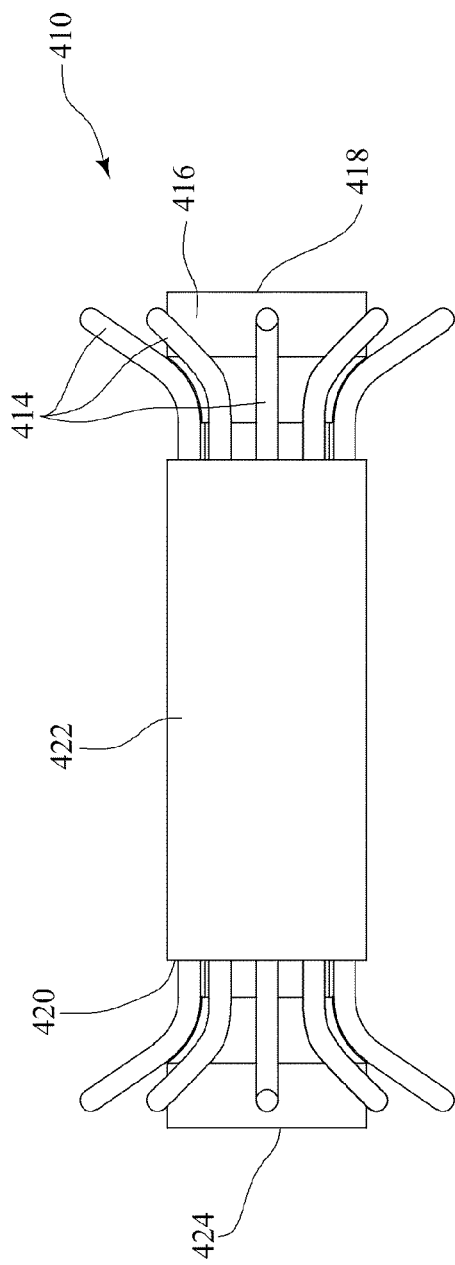
FIG. 30 is a side view of the device of FIG. 28, illustrating the rods at both ends in a deployed position.
Figure 32:
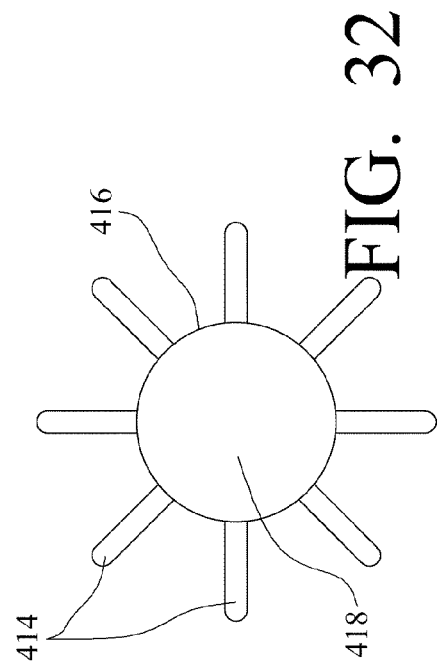
FIG. 32 is an end view of the device of FIG. 28, illustrating the rods in a deployed position.
Figure 31:
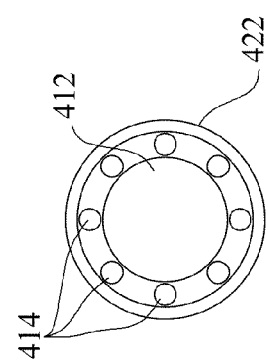
FIG. 31 is a sectional view of the device of FIG. 28 taken along line 31-31 of FIG. 28.

As a further refinement, and as shown in FIG. 27, it should also be recognized that the rear portions of the rods 314 could also be expanded outward to better fix the position of the device 310 within the femur 40. To do so, after the rods 314 have been advanced as described above into the deployed position shown in FIGS. 24 and 25, a second end cap 324 with links 326 and a construction similar to that of the first end cap 316 would be used to capture the free ends of the rods 314 and force them to flare out into the surrounding bone in a similar manner.

Referring now to FIGS. 28-32, another exemplary device 410 includes a main shaft 412; a plurality of rods 414 surrounding the main shaft 412; a first end cap 416 located at a first end 418 of the device 410 and having a flared circumferential surface 419; and a sleeve 422 for maintaining the positioning of the rods 414 relative to the main shaft 412. When the device 410 is inserted into the hole 100 (as shown in FIG. 6), each of the rods 414 is individually advanced towards the first end 418. As each rod 414 is advanced, its distal end contacts the flared circumferential surface 419 of the first end cap 416, which forces the rod 414 outward into the surrounding bone. In turn, each of the rods 414 is similarly advanced such that all of the rods 414 are flared outward and away from the main shaft 412, resulting in the deployed position shown in FIG. 29.

As a further refinement, this exemplary device 410 may include a second end cap 424 at the second end 420 of the device 410. This second end cap 424 defines a screw-receiving channel (not shown) for receiving a threaded portion 412a of the main shaft 412. As the second end cap 424 is rotated to advance toward the first end cap 416, the flared circumferential surface of the second end cap 424 engages the free ends of the rods 414, forcing the rods 414 outward and into the surrounding bone.

As noted above, for any device implanted in the femur, it is important to prevent any stress shielding, i.e., in bone loss around the device due to the relative unloading of the bone from the load-sharing nature of the stiffer metal. With respect to the device of the present invention, and irrespective of the exemplary embodiment chosen for implantation, the device will not cause stress shielding of the bone surrounding the device because of the orientation of the device along a generally horizontal axis 54 that is substantially perpendicular to the long axis 52 of the femoral shaft 47 of the femur 40. Referring again to FIG. 6, because the load that causes the fracture is not along the axis of the normal load-bearing vector 48, there is little danger of the device causing a stress shielding problem over the course of normal activity as the normal loading trajectory will not result in a significant amount of load-bearing or load-sharing with the device. Instead, the device will be incorporated into the bony architecture of the femur 40 and provide stiffness to resist fracture initiation in the event of a loading event along its axis (i.e., a fall to the side causing the loading shown in FIG. 5). In addition, it is preferred that the device should avoid making a continuous connection between the load-bearing dome of the femoral head 42 and the cortex of femoral shaft 47 to further avoid stress shielding.

With respect to each of the exemplary embodiments described above, it is preferred that the device in its deployed position should have as low a profile to the lateral surface of the greater trochanter as possible to avoid any irritation and discomfort to the patient. That being said, as a further refinement, it is contemplated that a portion of the device could extend from the insertion point (outside of the bone) and be provided with an enlarged head, so as to prevent any crushing of the bone from an impact to the greater trochanter at the insertion point.

With respect to each of the exemplary embodiments described above, the device is intended to be stiffer than the surrounding bone, and thus, it is preferred that the device be made of a metal (such as titanium, a nickel-titanium alloy, stainless steel, or a memory metal) or another suitably stiff material.

With respect to each of the exemplary embodiments described above, it is also contemplated that hydroxyapatite or other bioactive coatings or porous coatings could be applied to the device for improving the bond between the femur and the device. Such coatings would improve the bond/interface strength between the device and the surrounding bone, so a greater percentage of the load would pass through the device rather than to the surrounding bone of the femur. The increased strength would further improve the ability of the device to stiffen and strengthen the load pathway through the femur.

With respect to each of the exemplary embodiments described above, it is also contemplated that the device could be used in concert with injectable cements, bone grafts, or bone graft substitutes. For example, through the use of an injectable cement, the load-bearing capacity of the device and surrounding bone could be increased. Such an injectable cement could be injected before implantation of the device or could be injected post-implantation through the device, with the device serving as a conduit for such injection and delivery. Furthermore, various injectable reinforcing material or injectable material for stimulating or facilitating bone growth could be used in concert with the device of the present invention.

With respect to each of the exemplary embodiments described above, it is also contemplated that the device could release bioactive materials, drugs, bone healing or regeneration agents, and/or bone morphogenetic proteins to stimulate the surrounding bone to become denser or thicker, thus improving fracture resistance at the critical (femoral neck) site. It is also contemplated that the implanted device could act as a conduit or reservoir for the subsequent injection or delivery of bioactive materials or drugs to the critical site in the femur.

One of ordinary skill in the art will also recognize that additional embodiments are possible without departing from the teachings of the present invention or the scope of the claims which follow. This detailed description, and particularly the specific details of the exemplary embodiments disclosed therein, is given primarily for clarity of understanding, and no unnecessary limitations are to be understood therefrom, for modifications will become obvious to those skilled in the art upon reading this disclosure and may be made without departing from the spirit or scope of the claimed invention.

What is claimed is:

1. A device for preventing a hip fracture, comprising:
a shaft having a first end and a second end, wherein the shaft is configured to be positioned in a hole of a predetermined depth in a femur, which is characterized, in part, by a femoral head, a greater trochanter, a femoral neck, and a femoral shaft, said hole extending from the greater trochanter to the femoral head, the shaft having a length such that, upon positioning of the shaft in the hole, the first end of the shaft is positioned in the femoral head and the second end is positioned in the greater trochanter; and
an expanding means for engaging the femoral head at the first end, the expanding means comprising a plurality of portions, each of the plurality of portions having a distal end adjacent to the first end of the shaft, and each of the plurality of portions configured to separately flare radially outward;
wherein the device is configured to be oriented along a generally horizontal axis that is substantially perpendicular to a long axis of the femoral shaft; and
wherein, upon deployment of the expanding means, each distal end of each of the plurality of portions of the expanding means flares radially outward independently of each other distal end of the plurality of portions to collectively create an enlarged bearing face at the first end that engages the femoral head, such that the device is configured to buttress the femur and resist compressive stress along the generally horizontal axis.

2. The device as recited in claim 1, in which said hole terminates near an axis defining a normal load-bearing vector of the femur.

3. The device as recited in claim 1, in which a portion of the shaft is adjacent to a superior wall of the femoral neck upon positioning of the shaft in the hole.

4. The device as recited in claim 1, wherein said expanding means includes:
a plurality of rods surrounding the shaft;
a first end cap located at the first end of the shaft; and
a plurality of links, each said link connecting one of the plurality of rods to the first end cap, with each said link being pivotally connected to the first end cap at one end about a pivot axis;

wherein, when the device is positioned in said hole, each of the plurality of rods is advanced towards the first end of the shaft, causing the respective link to rotate about the respective pivot axis, such that there is a controlled flaring of each rod into surrounding bone.

5. The device as recited in claim 4, in which each said link defines a cavity near its opposite end for receiving a distal end of one of the rods, such that when each of the plurality of rods is advanced towards the first end of the shaft, the distal end of the respective rod presses into the cavity defined by the respective link, causing the respective link to rotate about the respective pivot axis.

6. The device as recited in claim 4, and further comprising a sleeve for maintaining the positioning of the rods relative to the shaft.

7. The device of claim 1, wherein the enlarged bearing face has a cross-sectional area greater than about 500 mm$^2$.

8. A device for preventing a fracture in a femur, which is characterized, in part, by a femoral head, a greater trochanter, a femoral neck, and a femoral shaft, the device comprising:

a shaft having a first end and a second end, wherein the shaft is configured to be positioned in a hole of a predetermined depth in the femur, said hole extending along a generally horizontal axis from the greater trochanter to the femoral head and terminating near an axis defining a normal load-bearing vector of the femur, the shaft having a length such that, upon positioning the shaft in the hole, the first end is positioned in the femoral head and the second end is-positioned in the greater trochanter; and an expanding means for engaging the femoral head at the first end, the expanding means comprising a plurality of portions, each of the plurality of portions having a distal end adjacent to the first end of the shaft, and each of the plurality of portions configured to separately flare radially outward;

wherein, upon deployment of the expanding means, each distal end of each of the plurality of portions of the expanding means flares radially outward independently of each other distal end of the plurality of portions to collectively create an enlarged bearing face at the first end that engages the femoral head, such that the device is configured to buttress the femur and resist compressive stress along the generally horizontal axis.

\* \* \* \* \*

UNITED STATES PATENT AND TRADEMARK OFFICE
CERTIFICATE OF CORRECTION

| | | |
|---|---|---|
| PATENT NO. | : 9,452,003 B2 | Page 1 of 1 |
| APPLICATION NO. | : 12/508350 | |
| DATED | : September 27, 2016 | |
| INVENTOR(S) | : Voor et al. | |

It is certified that error appears in the above-identified patent and that said Letters Patent is hereby corrected as shown below:

On the Title Page

Item (12) delete "Voor" and insert --Voor et al.--.
Item (75) Inventor, should read:
--(75) Inventors: Michael J. Voor, Louisville, KY (US); Robert Burden, Louisville, KY (US)--.

Signed and Sealed this
Sixth Day of June, 2017

Michelle K. Lee
*Director of the United States Patent and Trademark Office*